United States Patent [19]

Seth

[11] Patent Number: 4,540,572

[45] Date of Patent: Sep. 10, 1985

[54] GEL-LIKE OINTMENT CONTAINING INDOMETACIN

[75] Inventor: Pyare Seth, Aesch, Switzerland

[73] Assignee: Mepha AG, Aesch, Switzerland

[21] Appl. No.: 566,578

[22] Filed: Dec. 29, 1983

[30] Foreign Application Priority Data

Aug. 29, 1983 [CH] Switzerland ................. 4726/83

[51] Int. Cl.$^3$ ................. A61K 31/40; A61K 31/736
[52] U.S. Cl. ................. 424/81; 514/420; 514/887
[58] Field of Search ................. 424/81, 274

[56] References Cited

PUBLICATIONS

Chem. Abst. 95-103322x, (1982).

Chem. Abst. 93-13094d, (1980).

*Primary Examiner*—Stanley J. Friedman
*Attorney, Agent, or Firm*—Ladas & Parry

[57] ABSTRACT

In addition to indometacin, the gel-like ointment for the topical treatment of inflammation contains a water-soluble cellulose ether or/and a polyacrylic acid, the carboxyl groups of which are neutralized by a water-soluble amine, plus water and ethanol or isopropanol; the components are present in the ratio of amounts suitable for forming a gel. Determination of the level of indometacin in the serum of humans has shown that the absorption through the skin of the active compound from the new ointment is significantly higher than that from the most closely related products.

1 Claim, No Drawings

GEL-LIKE OINTMENT CONTAINING INDOMETACIN

Investigations have been carried out for some time with the object of producing a product based on indometacin for the topical treatment of inflammation. This is because the poor solubility of the active compound in water and customary media on the one hand, and a lack of its absorption through the human skin from the conventional ointment bases on the other hand, stand in the way of the necessary effectiveness of a product of this type.

In order to overcome these difficulties, the use of methyl salicylate as vehicle and solubilizer has been proposed, first in German Patent Specification No. 2,103,833; it has said to increase the absorption at the same time. Such a product comprises, for example, the following:

50% ethanol
10% methyl salicylate
15% polysorbate 80
5% diisopropyl adipate and
20% water and contains 2.0 mg of indometacin per milliliter of methyl salicylate.

German Offenlegungsschriften No. 2,827,018 and 3,006,024 point in another direction, according to each of these glycol or a polyalkylene glycol being used as vehicle and solubilizer. In the second Offenlegungsschrift mentioned, the vehicle is composed of a preponderant amount of a polyalkylene glycol and a smaller amount of a polyethylene glycol $C_{10}$–$C_{14}$-alkyl ether. A typical product of this type contains, in addition to indometacin, essentially polyethylene glycols, polyethylene glycol dodecyl ether and water in the weight ratio 75:5:7.4 for ointment and 20:2:73 for a gel; polyacrylic acid and triethanolamine are used for the formation of the gel.

A gel is likewise described in German Offenlegungsschrift No. 2,827,018; the vehicle comprises a glycol, in particular propylene glycol, butylene glycol or polyethylene glycol, an alcohol and water. The gel-forming agents are cellulose and cellulose derivatives or the amine salt of a carboxyvinyl polymer (polyacrylic acid). A gel of this type is composed of, for example, the following:

indometacin: 1.0 g
carboxyvinyl polymer: 1.0 g
hydroxyethylcellulose: 1.0 g
polyethylene glycol 300: 10.0 g
ethanol: 30.0 g
diisopropyl adipate: 2.0 g
diisopropylamine: 0.9 g
water: 54.1 g Surprisingly, it has now been found that by omitting any glycol or polyalkylene glycol from the mixture described above, a gel-like ointment is obtained, and this not only has effectiveness on topical use but is even significantly superior to the most closely related product in this respect.

The new product according to the invention contains indometacin, a water-soluble cellulose ether or/and a polyacrylic acid, the carboxyl groups of which are neutralized by a water-soluble amine, plus water and ethanol or isopropanol. The said components are present in a ratio of amounts suitable for the formation of a gel.

The water-soluble cellulose ether and the polyacrylic acid in the product function as gel-forming agents, the intention being that the acid groups in the latter be neutralized by the basic group(s) of the water-soluble amine. Possible examples of an amine of this type are methylamine, dimethylamine, ethylamine, diethylamine, propylamine, isopropylamine, diisopropylamine, cyclohexylamine, benzylamine, guanidine, pyrrolidine, piperidine, morpholine, arginine, lysine, ethanolamine, diethanolamine, diisopropanolamine or triethanolamine. The lower aliphatic amines which are liquid at room temperature are preferred, for example diisopropanolamine or diethylamine. The amine is advantageously used in excess over the stoichiometric ratio to the carboxyl groups in the polyacrylic acid.

The ointment should have a physiologically tolerated pH; it is advantageously adjusted to a pH in the range from 6.7 to 7.0, preferably to pH 6.8. It is possible to add the necessary amount of the abovementioned water-soluble amine to adjust the pH.

Of the polyacrylic acids, also called carboxyvinyl polymers, it is possible to use, in particular, those which are obtainable under the tradename Carbopol, for example Carbopol 941, Carbopol 934 or Carbopol 940, which have a mean molecular weight of 1,250,000, 3,000,000 and 4,000,000 respectively (manufactured by Goodrich Chemical Co., Cleveland, OH/USA).

Examples of water-soluble cellulose ethers which may be mentioned are methylcellulose, ethylcellulose, carboxymethylcellulose (also called cellulose glycolate), hydroxyethylcellulose, hydroxypropylcellulose and celluloseethanesulfonic acid. In this context, see also Ullmanns Encyklopädie der technischen Chemie (Ullmann's Encyclopedia of Industrial Chemistry), 4th edition, volume 9, pages 192–212, Verlag Chemie, Weinheim, FRG, 1975.

The ointment advantageously also contains a superfatting agent in order to make up for the possibility of the skin drying out under the action of ethanol or isopropanol. Examples of superfatting agents to be used are ethyl caproate, ethyl laurate, diethyl sebacate and diisopropyl adipate; the latter is preferred.

The product preferably contains, for 1.0 part by weight of indometacin, the following:

from 0.5 to 2.0 parts by weight of polyacrylic acid and/or water-soluble cellulose ether
from 30 to 50 parts by weight of ethanol or isopropanol
from 1.0 to 5.0 parts by weight of superfatting agent
(from 1.0 to 2.0 parts by weight of water-soluble amine when a polyacrylic acid is used)
and sufficient water to form 100 parts by weight.

Where desired, the ointment can also contain an odor-improving agent (flavoring agent). Particularly suitable examples of this are ethereal oils, such as lavender oil, thyme oil, the citrus oils, for example bergamot oil, lemon oil, the conifer needle oils, such as cypress oil, pine-needle oil and dwarf-pine oil, also citronella oil, eucalyptus oil, camphor, thymol etc. It is possible to add, for example, 0.04% by weight of the conifer needle oils or, for example, 0.05% by weight of camphor or thymol.

In as far as the composition of the ointment fits in with the invention, the product can additionally contain one or more other agents which are able to supplement or assist an antiphlogistic or antiinflammatory effect on topical use, and which in the form of a gel-like ointment are absorbed through the skin; examples of these which may be mentioned are analgesics and muscle relaxants. Of course, these types of new products likewise fall within the scope of the present patent.

In order to test the effectiveness of the product, the bioavailability of indometacin was determined after external application of the ointment, ie. that amount of indometacin which appears in the blood after absorption through the skin. The investigations were carried out on 6 volunteer subjects using a 1% strength ointment according to the present Example 3; the reference or comparison product included in the investigation was a 1% strength commercial product according to German Offenlegungsschrift No. 2,827,018.

Before starting the trial, the nature, aims and extent of the trial were explained to the subjects and they all gave their consent to participate in the trial. They then underwent specialist examination (with comprehensive laboratory, drug and alcohol screening) and were classified as healthy.

The single-dose crossover trial entailed the subjects having 3 g (which corresponds to a content of indometacin of 30 mg) of the new product or of the comparison product applied to an exactly defined site on the lower arm.

After a period of 7 days without treatment, the subjects in the crossover trial received the other product in each case.

Blood was sampled for the determination of the level of indometacin in the serum immediately before application of the products and 15', 30', 45', 1h, 1h30', 2h, 3h, 4h, 5h, 8h, 12h and 24h thereafter.

The levels in the serum, and the means, standard deviations and mean standard errors of these are indicated in Tables 1 and 2, and the pharmacokinetic parameters are to be found in Tables 3 and 4.

TABLE 1

Levels in the serum of indometacin from the new product concentration in ng/ml

| Subject | 0 h | 15' | 30' | 45' | 1 h | 1 h 30' | 2 h | 3 h | 4 h | 5 h | 8 h | 12 h | 24 h |
|---|---|---|---|---|---|---|---|---|---|---|---|---|---|
| 1 | 0 | 0 | 7.3 | 6.9 | 8.3 | 3.5 | 7 | 2.7 | 5.1 | 5.3 | 3.2 | 4.9 | 2.5 |
| 2 | 1.4 | 0 | 8.3 | 4.02 | 0 | 0 | 7.2 | 3.8 | 16.2 | 7.3 | 5.7 | 0 | 1.7 |
| 3 | 1.2 | 2,7 | 0 | 0 | 0 | 0 | 0 | 0 | 0 | 0 | 0 | 0 | 10.1 |
| 4 | (1.00 | 5,4 | 0 | — | 7.2 | 0 | 8.3 | 11.1 | 13.4 | 11.5 | 13 | 6 | 6.4 |
| 5 | 5.2 | 5,3 | 1.6 | 4.9 | 2.8 | 1.9 | 4.1 | 1.4 | 2.5 | 3.4 | 3.4 | 5.6 | 4.9 |
| 6 | 2.6 | 4,5 | 4.7 | 1.5 | 1.3 | 2 | 3.7 | (1.00 | 2.2 | 4.4 | 4 | 4.6 | 1.5 |
| mean | 2.08 | 2,98 | 3.65 | 3.46 | 3.27 | 1.23 | 5.05 | 3.8 | 6.57 | 5.32 | 4.88 | 3.52 | 4.52 |
| sdev | 1.97 | 2.51 | 3.66 | 2.74 | 3.64 | 1.47 | 3.07 | 4.32 | 6.64 | 3.87 | 4.39 | 2.77 | 3.35 |
| sem | 0.88 | 1.02 | 1.49 | 1.23 | 1.49 | 0.6 | 1.25 | 1.93 | 2.71 | 1.58 | 1.79 | 1.13 | 1.37 | sdev: standard deviation
sem: standard error of the mean
( = value below the detection limit
— = sample lost or destroyed

TABLE 2

Level in the serum of indometacin from the reference product concentration in ng/ml

| Subject | 0 h | 15' | 30' | 45' | 1 h | 1 h 30' | 2 h | 3 h | 4 h | 5 h | 8 h | 12 h | 24 h |
|---|---|---|---|---|---|---|---|---|---|---|---|---|---|
| 1 | 0 | 2 | 2.6 | 6.2 | 1.4 | — | 1.3 | 2.7 | 0 | 0 | 0 | 6.8 | — |
| 2 | — | 0 | (1.00 | 5.9 | 2.7 | 2.3 | 2.2 | (1.00 | 1.5 | 0 | 0 | 0 | 6.3 |
| 3 | 5.2 | 8.5 | 2.8 | 3.3 | 2.3 | 5.2 | 2.2 | (1.00 | 3.1 | 0 | 0 | — | 0 |
| 4 | — | 2.6 | (1.00 | 0 | 2.5 | 0 | (1.00 | 0 | 1.9 | (1.00 | 2.8 | 6 | 0 |
| 5 | 0 | 7.8 | 2.9 | 6.7 | 7.1 | 5 | 5 | 6.1 | 0 | 7.3 | 7.2 | 8.9 | 0 |
| 6 | 0 | 1.7 | 6 | 1.1 | 0 | 1 | 1 | (1.00 | 1.9 | 1 | 2.5 | 4.3 | 0 |
| mean | 1.3 | 3.77 | 3.58 | 3.87 | 2.67 | 2.7 | 2.34 | 2.93 | 1.4 | 1.66 | 2.08 | 5.2 | 1.26 |
| sdev | 2.6 | 3.51 | 1.62 | 2.85 | 2.39 | 2.34 | 1.58 | 3.06 | 1.21 | 3.18 | 2.82 | 3.34 | 2.82 |
| sem | 1.3 | 1.43 | 0.81 | 1.16 | 0.98 | 1.05 | 0.71 | 1.76 | 0.49 | 1.42 | 1.15 | 1.5 | 1.26 | sdev: standard deviation
sem: standard error of the mean
( = value below the detection limit
— = sample lost or destroyed

TABLE 3

Pharmacokinetic parameters of the new product, calculated from the levels in the serum (Table 1)

| Subject | AUC | Cmax | Tmax |
|---|---|---|---|
| 1 | 97.46 | 8.3 | 1 |
| 2 | 73.41 | 16.2 | 4 |
| 3 | 61.43 | 10.1 | 24 |
| 4 | 189.9 | 13.4 | 4 |
| 5 | 105.5 | 5.6 | 12 |
| 6 | 81.01 | 4.7 | 0,5 |
| mean | 101.4 | 9.717 | 7.583 |
| stdev | 46.18 | 4.469 | 9.036 |
| sem | 18.85 | 1.825 | 3.689 |
| Unit: | hxng/ml | ng/ml | h |

AUC: area under the curve
Cmax: maximum concentration
Tmax: time at which concentration is at maximum

TABLE 4

Pharmacokinetic parameters of the reference product, calculated from the levels in the serum (Table 2)

| Subject | AUC | Cmax | Tmax |
|---|---|---|---|
| 1 | 21.18 | 6.8 | 12 |
| 2 | 47.18 | 6.3 | 24 |
| 3 | 15.16 | 8.5 | 0.25 |
| 4 | 65.54 | 6 | 12 |
| 5 | 130.4 | 8.9 | 12 |
| 6 | 51.95 | 6 | 0.5 |
| mean | 55.23 | 7.083 | 10.13 |
| stdev | 41.45 | 1.292 | 8.868 |
| sem | 16.92 | 0.5275 | 3.62 |

TABLE 4-continued

| Pharmacokinetic parameters of the reference product, calculated from the levels in the serum (Table 2) | | | |
|---|---|---|---|
| Subject | AUC | Cmax | Tmax |
| Unit: | hxng/ml | ng/ml | h |

AUC: area under the curve
Cmax: maximum concentration
Tmax: time at which concentration is at maximum As can be seen from Tables 3 and 4, the AUC for the new product was 101.4 hxng/ml, and the figure for the reference product was 55.2 hxng/ml. The maximum concentration for the new product was 9.7 ng/ml and that for the reference product was 7.1 ng/ml.

The relative bioavailability of the product according to the invention compared with the reference product is 183.6%, and it is thus a factor of 1.8 better.

Comparison of the compositions of the two products shows that this difference in effectiveness can only be due to the omission of the glycol or polyalkylene glycol. This result was all the more unexpected because propylene glycol, for example, is frequently employed as a solvent for active compounds in medicaments for external application and carries the dissolved active compound with it through the barrier of the horny layer of the skin (M. Gloor, Pharmakologie dermatologischer Externa (The Pharmacology of Topical Dermatological Products) published by Springer, Berlin, Heidelberg, New York, 1982, pages 7–8 and 42). Moreover, propylene glycol and polyethylene glycol are customarily used as water-soluble bases for ointments (L. S. Goodman and A. Gilman, The Pharmacological Basis of Therapeutics, 5th edition, Macmillan Publishing Co. Inc., New York 1975, page 947), and not only for ointments containing other active compounds but, in particular, even for ointments containing indometacin (European Patent Application No. 55,029).

It is best to take advantage of the possibility of testing the therapeutic effect of the new product on human patients rather than by pharmacological tests in vitro or on living animals. Not until it has been used therapeutically in concrete cases in daily life, with assessment of the results by the treating physicians, will it be possible to draw final conclusions in respect of the effectiveness.

For this reason, the effectiveness and the tolerance of the product according to Example 4 (under the protected tradename Bonidon Gel) have been investigated in a multicenter phase IV study, which has been running since January 1983, of the treatment in practice of inflammatory and degenerative rheumatic diseases and traumas of the joints and soft tissues in 153 patients.

The intention in this trial was that Bonidon Gel should, in accordance with the information for use, be applied thinly to a large area over the affected part of the body 2–3 times daily. The intention was that therapy should not last longer than 3 weeks. The progress of the disease was to be checked after 1, 2 and, where appropriate, 3 weeks. The intensity of the symptoms was assessed by the physician and entered in the record sheet using the classes severe, moderate, slight and free of symptoms.

It was necessary to exclude 24 patients because the conditions of the trial were not observed, insufficient data was collected for one other patient, and one discontinued treatment because of an undesired effect of the medicament; thus, the data for 127 patients were evaluated for the report. Of these, 39 suffered from degenerative joint diseases, 16 from non-articular rheumatism, 43 had suffered traumatic injuries and 29 suffered from other complaints.

The parameters which were assessed were pain, swelling and functional impairment. 19% of the patients were treated for one week, 33.2% for two weeks and 47.8% for three weeks. At the end of therapy, the symptoms had completely disappeared in 62.2% of the cases, and the symptoms had improved in 33.4%.

The product was very well tolerated. Only 4.7% of the patients reported itching, reddening or burning of the treated areas of skin, the undesired effects being denoted mild and transient in the majority of cases.

Examples of the composition and the preparation of the product according to the invention are given in the following text; the amounts given relate to parts by weight.

TABLE 5

| No. | Substance | 1 | 2 | 3 | 4 |
|---|---|---|---|---|---|
| 1 | indometacin | 1.0 | 1.0 | 1.0 | 1.0 |
| 2 | Carbopol (R) 941 | — | 1.0 | 1.5 | 2.0 |
| 3 | hydroxypropylcellulose Klucel(R)* | 2.0 | 0.5 | — | — |
| 4 | diisopropanolamine | 1.0 | 1.5 | 1.8 | 2.0 |
| 5 | 95% ethanol | 40.0 | 40.0 | 35.0 | 50.0 |
| 6 | diisopropyl adipate | 3.0 | 4.0 | 5.0 | 5.0 |
| 7 | purified water ad | 100.0 | 100.0 | 100.0 | 100.0 |

*manufactured by Hercules Inc., Wilmington (DE/USA)

Example 1

| | |
|---|---|
| (4) is dissolved in 10 parts of water (7) | solution A |
| (5) and (6) are mixed together, (1) is dissolved in this mixture with stirring and sufficient solution A is added slowly until a pH of 6.9 is reached | solution B |
| (3) is mixed with 20 parts of water (7), a homogeneous suspension is produced from this, solution B is added slowly, and the mixture is thoroughly stirred | gel C |
| the gel is allowed to stand overnight and is finally adjusted to the desired weight by adding water (7) | gel D |

Example 2

| | |
|---|---|
| (4) is dissolved in 10 parts of water (7) | solution A |
| (5) and (6) are mixed together, (1) is dissolved in this mixture with stirring, and sufficient solution A is added slowly until a pH of 6.8 is reached | solution B |
| (3) is mixed with 20 parts of water (7), a homogeneous suspension is produced from this, solution B is slowly added, and the mixture is thoroughly mixed and allowed to stand overnight | gel C |
| (2) is dissolved in 20 parts of water (7) by allowing it to swell for some time and stirring until a homogeneous composition is formed, and this is mixed slowly, with continuous stirring, into gel C in order to form a homogeneous gel, and the pH of the gel is adjusted to 6.8 by slowly adding solution A, and finally the mixture is adjusted to the desired weight by adding water (7) | gel D |

Examples 3 and 4

| | |
|---|---|
| (4) is dissolved in 10 parts of water (7) | solution A |
| (1) is dissolved in a mixture of (5) and (6) with the formation of a clear solution, and sufficient solution A is slowly added until a pH of 6.8 is reached | solution B |
| (2) is mixed with 20 parts of water (7), allowed to swell for some time and stirred until a homogeneous composition is formed, and solution A is added, with stirring, until the pH is adjusted to 6.8 | gel C |
| solution B is mixed slowly, with continuous stirring, into gel C in order to form a | gel D |

Example 5

| | |
|---|---|
| 2.0 g of diisopropanolamine are dissolved in 10 ml of purified water | solution A |
| 1.0 g of indometacin is dissolved in a mixture of 50 g of isopropanol and 5 g of diisopropyl adipate with the formation of a clear solution, and sufficient solution A is added slowly until a pH of 6.9 is reached | solution B |
| 2.0 g of carboxymethylcellulose are mixed with 20 ml of purified water, allowed to swell for some time and stirred until a homogeneous composition is formed, and solution A is added, with stirring, until the pH is adjusted to 6.9 | gel C |
| solution B is mixed slowly, with continuous stirring, into gel C in order to form a homogeneous gel, and finally the mixture is adjusted to a weight of 100 g by adding purified water | gel D |

Example 6

| | |
|---|---|
| 2.0 g of diisopropanolamine are dissolved in 10 ml of purified water | solution A |
| 1.0 g of indometacin is dissolved in a mixture of 50 g of isopropanol, 5 g of diisopropyl adipate and 0.07 g of pine-needle oil with the formation of a clear solution, and sufficient solution A is added slowly until a pH of 6.9 is reached | solution B |

The further steps are carried out exactly as in Example 5 and they lead to 100 g of gel which correspond to that according to Example 5 apart from the odor and the content of pine-needle oil (0.04% by weight).

I claim:

1. A product containing indomethacin, which is in the form of a gel-like ointment for the topical treatment of inflammation and which contains for 1.0 part by weight of indomethacin, 0.5 to 2.0 parts by weight of a water-soluble cellulose other or/and of a polyacrylic acid, the carboxyl groups of which are neutralized by a water-soluble amine in a greater than stoichiometric ratio to said carboxyl groups, 30 to 50 parts by weight of ethanol or isopropanol, 1.0 to 5.0 by weight of a superfatting agent, and water to complete 100 parts by weight, said product being essentially free of any glycol or polyalkylene glycol.

* * * * *